US006355839B1

(12) United States Patent
Onopchenko

(10) Patent No.: US 6,355,839 B1
(45) Date of Patent: Mar. 12, 2002

(54) ALKYLATION OF DIPHENYLAMINE WITH POLYISOBUTYLENE OLIGOMERS

(75) Inventor: Anatoli Onopchenko, Concord, CA (US)

(73) Assignee: Chevron U.S.A., Inc., San Ramon, CA (US)

( * ) Notice: Subject to any disclaimer, the term of this patent is extended or adjusted under 35 U.S.C. 154(b) by 0 days.

(21) Appl. No.: 09/944,906

(22) Filed: Aug. 31, 2001

(51) Int. Cl.$^7$ .............................................. C07C 209/68

(52) U.S. Cl. ....................... 564/409; 564/433; 564/308; 564/309; 544/102; 544/103; 544/35

(58) Field of Search ................................ 564/409, 433, 564/308, 309; 544/102, 103, 35

(56) References Cited

U.S. PATENT DOCUMENTS

| 2,943,112 | A | 6/1960 | Popoff et al. ................ 260/576 |
| 3,452,056 | A | 6/1969 | Sundholm .................... 260/390 |
| 4,152,499 | A | 5/1979 | Boerzel et al. ............. 526/52.4 |
| 4,605,808 | A | 8/1986 | Samson ........................ 585/525 |
| 4,824,601 | A | 4/1989 | Franklin ...................... 252/401 |
| 5,672,752 | A | 9/1997 | Lai et al. ..................... 564/409 |
| 5,750,787 | A | 5/1998 | Lai et al. ..................... 564/409 |
| 6,204,412 | B1 | 3/2001 | Lai .............................. 564/409 |

*Primary Examiner*—Samuel Barts
(74) *Attorney, Agent, or Firm*—Steven R. Ellinwood

(57) ABSTRACT

A process for preparation of alkylated diphenylamine antioxidant which comprises alkylating diphenylamine with a polyisobutylene in the presence of a clay catalyst, wherein the polyisobutylene has an average molecular weight in the range of 120 to 600 and wherein the polyisobutylene contains at least 25% methylvinylidene isomer.

27 Claims, No Drawings

ALKYLATION OF DIPHENYLAMINE WITH POLYISOBUTYLENE OLIGOMERS

FIELD OF THE INVENTION

This invention relates to a process for preparation of alkylated diphenylamine that is liquid at room temperature. More specifically, this invention relates to a process for alkylation of diphenylamine (DPA) with polyisobutylene (PIB) oligomers having a molecular weight in the range of 120 to 600 and having a methylvinylidene content of at least 25%. Preferably, the reaction is carried out in the presence of a clay catalyst, but other types of catalysts can be used. The alkylated diphenylamine prepared by the disclosed process exhibits excellent antioxidant characteristics in lubricating oil formulations.

BACKGROUND OF THE INVENTION

Alkylated diarylamines, such as alkylated diphenylamine, are well known in the art to be effective stabilizers or antioxidants in a wide variety of organic materials, including, among other organic materials, mineral oil derived lubricants and synthetic lubricants. In this use, light colored, liquid (at about 20° C.) products are desirable for a number of practical reasons.

Alkylation of diarylamines, such as diphenylamine, with olefins in the presence of suitable alkylation catalysts is well known in the art. For example, U.S. Pat. No. 2,943,112 (Popoff et al.) teaches a two step process whereby alkylation of diphenylamine with relatively unreactive olefins, such as secondary alkenes (column 4, line 9–23), is followed by an alkylation reaction with more reactive olefins to scavenge the unreacted diphenylamine. Popoff also teaches the use of acid activated clay as an alkylation reaction catalyst to achieve the desired light color. (See also, U.S. Pat. No. 3,452,056 wherein acid clay, AlCl$_3$ and ZnCl$_2$ are mentioned as suitable catalysts).

Similarly, Franklin, U.S. Pat. No. 4,824,601, (column 1, lines 26–67), teaches the use of acidic clay catalysts to alkylate diphenylamine and further teaches that a light colored, liquid product may be prepared by process comprising reacting the alkylation reactants within certain molar ratios and temperature ranges for a time sufficient to ensure the alkylated product contains less than 25% dialkylated diphenylamine. This low proportion of dialkylated diphenylamine is disclosed as necessary to avoid the formation of crystallized, solid products, which are not advantageous in terms of ease of handling, transportation, storage and incorporation into the substrate to be stabilized.

More recently, addressing the same problem; that is, preparing an effective antioxidant from diphenylamine that is liquid at room temperature, Lai in U.S. Pat. Nos. 5,672,752 (Lai 1) and 5,750,787 (Lai 2), teaches processes for alkylating diphenylamine with linear alpha olefins (Lai 1) and diisobutylene (Lai 2) in the presence of a clay catalyst. These processes, as disclosed, selectively result in a higher proportion of monoalkylated diphenylamine and a lower proportion of unsubstituted diphenylamine and/or disubstituted or polysubstituted diphenylamines. These patents further disclose that to obtain the desired liquid product, the ratio of olefin to diphenylamine in the reaction mixture, together with reaction temperature and time is important to give a product mixture with less than 25% dioctyldiphenylamine, less than 25% unreacted diphenylamine and greater than 50% by weight monooctyldiphenylamine based on the total weight of the diphenylamine and alkylated DPA.

In U.S. Pat. No. 6,204,412 (Lai 3) Lai discloses yet another method of alkylating diphenylamine to obtain a light colored, liquid product, which comprises a two step method wherein, in the second step, a second olefin is added to the reaction mixture containing diphenylamine and diisobutylene (and/or an alpha-olefin of the disclosed formula) to scavenge or reduce the amount of unreacted diphenylamine in the product As with Lai 1 and Lai 2, specific mole ratio ranges, reaction temperatures and reaction times are disclosed as important to obtain the desired alkylated diphenylamine that is liquid at room temperature.

SUMMARY OF THE INVENTION

The present invention relates to the preparation of alkylated diphenylamine and other alkylated aromatic amine antioxidant compositions using highly reactive polyisobutylenes as the alkylating reagent. Highly reactive polyisobutylenes (HR PIB) are valued for use in the lubricating oil additive industry and are commercially produced in the chemical industry. These valued HR PIB polymers are characterized by the presence of significant amounts of 2-methylvinylidene isomers, $R(CH_3)C=CH_2$ where R is a PIB residue, and a molecular weight preferably in the range of about 500 to 5000. Such 2-methylvinylidene polyisobutylenes are typically prepared using boron trifluoride catalysis. The preparation of such polyisobutylenes in which the methylvinylidene isomer comprises a high percentage of the total olefin composition is described in U.S. Pat. Nos. 4,152,499 and 4,605,808, the disclosures of which are incorporated herein by reference.

It is generally known by those skilled in the art that the commercial HR PIB production process described above generates a HR PIB distillate byproduct that; (i) contains mostly $C_8H_{16}$ to $C_{28}H_{56}$ oligomers (average $C_{14}H_{28}$), (ii) exhibits a relatively low average molecular weight of about 200 and, (iii) contains 2-methylvinylidene in the amount of at least about 25%. This low molecular weight distillate byproduct, which amounts to several percent of total HR PIB production, has little value and is typically sold as a waste product. Thus, a need exists in the chemical industry to develop a valuable use for the HR PIB distillate byproduct. It is the object of the present invention to meet this need by providing a novel process for preparation of a valuable alkylated diphenylamine antioxidant that is liquid at room temperature (about 20° C.) using the HR PIB distillate byproduct, or fractions thereof. For purposes of this invention, the term "polyisobutylene" refers to the HR PIB distillate byproduct and is further defined as comprising a mixture of highly reactive polyisobutylene oligomers, said mixture containing mostly $C_8H_{16}$ to $C_{28}H_{56}$ oligomers (average $C_{14}H_{28}$), exhibiting a molecular weight in the range of about 120 to about 600 (an average of about 200), containing a 2-methylvinylidene amount of at least about 25% and containing diisobutylene ($C_8$) in a fractional amount ranging from 0% to about 50%.

There are several advantages to using the presently employed polyisobutylene oligomers to alkylate diphenylamine and other aromatic amines, including, for example: (1) the alkylation reaction can be carried out at elevated temperatures under low pressure; (2) flexibility in utilizing a new, previously wasted feedstock, which can be comprised of specific carbon number fractions, a mixture of selected fractions or, most desirably, use of the total, unfractionated HR PIB distillate byproduct, with or without removal of inert solvent (2% to 10%); (3) the alkylation reaction can be carried out at relatively lower temperatures, which because of the greater reactivity afforded by the presence of 2-methylvinylidene results in a liquid alkylated product and no solid product as is usual in low temperature reactions with conventional diisobutylene, and; (4) milder, low temperature reaction conditions can be employed to control fragmentation.

Accordingly, the present invention provides a novel, one-step, process for the preparation of alkylated diphenylamine, which comprises reacting diphenylamine with polyisobutylene in the presence of a suitable alkylation catalyst at a suitable alkylation reaction temperature less than about 200° C., wherein said polyisobutylene contains at least about 25% of a methylvinylidene isomer and wherein the number average molecular weight of said polyisobutylene is in the range of about 120 to about 600 and wherein the mole ratio of said polyisobutylene to said diphenylamine is in the range of 1.0:1.0 to 4.0:1.0 and forming an alkylated diphenylamine product wherein said alkylated diphenylamine product is liquid at room temperature and atmospheric pressure.

In addition to diphenylamine, other aromatic amines are subject to alkylation by the disclosed process. Such other aromatic amines include, for example: N-phenyl-1-naphthylamine, N-phenyl-2-naphthylamine, p,p'-phenylenediamine, phenothiazine, phenoxazine, p-aminodiphenylamine, p-methylamino-diphenylamine and p-isopropylamino-diphenylamine.

DETAILED DESCRIPTION OF THE INVENTION

As noted above, the present invention provides a liquid alkylated diphenylamine, which is an effective antioxidant, by a process comprising alkylating diphenylamine with a polyisobutylene oligomer under suitable alkylation reaction conditions in the presence of a suitable alkylation catalyst. Generally, the polyisobutylene will have a number average molecular weight of about 120 to about 600, preferably in the range of about 150 to about 400, and more preferably in the range of about 160 to about 280 and a methylvinylidene content of at least about 25%, preferably in the range of about 25% to about 95%, more preferably in the range of about 40% to about 95%, and even more preferably in the range of about 60% to about 90%. Diisobutylene ($C_8$) may be present in the polyisobutylene in a fractional amount ranging from 0% to about 50% and preferably from about 10% to about 50%.

The use of clay as catalyst in the alkylation of diphenylamine is disclosed in U.S. Pat. No. 3,452,056, which describes the alkylation of diphenylamine with alpha-methylstyrene and related olefins with clay as the catalyst. In U.S. Pat. No. 2,943,112 and other prior art, clay is described as having several advantages including, for example: (1) as having the advantage of giving lighter colored product, (2) ease of removal by filtration after the reaction and (3) a lower degree of yellow color in the alkylated product. As a catalyst, clay and other Lewis Acids, such as $AlCl_3$ or $BF_3$ are generally taught as being interchangeable.(See, U.S. Pat. Nos. 3,452,056 and 5,672,752 at col. 3, ln. 3–6 and col. 1, ln. 33–41, respectively). More recently, U.S. Pat. Nos. 5,672,752; 5,750,787 and 6,204,412 identify certain commercially available clay catalysts, including; Filtrol™ and Retrol™ available from Engelhard; Fulcat™ 14, Fulmont™ 700C, Fulmont™ 237, and Fulcat™ 22B available from Laporte Industries; and Katalysator™ K10 available from Sud-Chemi. These clays may include acid activated or acid leached clays. The clay catalysts may contain some water as received. Removal of the water prior to use results in a lighter colored reaction product. Therefore, it is desirable to use clay with low water content or remove the water by heating the clay with a nitrogen sweep or with vacuum stripping. Acid activated clays are preferred; however, Lewis Acids such as $AlCl_3$ or $BF_3$, and $BF_3$ complexes of diethyl ether, phenol, including mixtures thereof with clay could be used as well. For purposes of this invention the preferred catalyst was determined to be Engelhard F-24 acid-activated clay (formerly Filtrol's Retrol clays).

Generally the reaction temperature for the alkylation reaction will be in range of about 125° C. to about 195° C., preferably in the range of about 135° C. to about 175° C., and more preferably in the range of about 155° C. to about 165° C. When using homogeneous acid catalysts, a lower temperature such as 75–100° C. may be used. The reaction can be carried out at a single temperature or, sequentially, at different temperatures.

The reaction pressure can range up to about 250 psi or higher, preferably below about 250 psi, and more preferably in the range of about 25 to 100 psi. Inert gas, such as nitrogen, can be used to minimize oxidation of products during reaction, but mostly to allow operation at higher temperatures with the lower boiling oligomers. A nitrogen or other inert gas atmosphere, in contrast to air, suppresses the formation of products that deactivate the clay catalyst. Other benefits of nitrogen pressure include higher rates of reaction, shorter reaction times, and enhanced formation of dialkylated DPA. The latter was achieved by preventing the loss of volatiles to the atmosphere.

The molar ratio of polyisobutylene to diphenylamine is normally in the range of about 1.0:1.0 to 4.0:1.0, preferably in the range of about 1.25:1.0 to 3.0:1.0, and more preferably in the range of about 1.5:1.0 to 2.8:1.0. Tables 1–3 in the Examples set forth the mole ratios of polyisobutylene to diphenylamine chosen for Examples 1–18. Other mole ratios may be chosen. The mole ratio chosen for the reaction will affect the degree of DPA conversion to alkylate. When diisobutylene is present in the polyisobutylene, preferably in the range of about 10 percent to about 50 percent, the mole ratio of diisobutylene:diphenylamine is less that about 0.6:1, preferably less than about 0.55:1 and more preferably less than about 0.45:1.

In practice it is difficult to take the reaction to the extinction of DPA because as the reaction continues the concentration of reactants diminishes and the rates become very slow. Generally, less than 5%, and more typically less than 1% DPA, is left unreacted in the product mixture. If desired, lower residual amounts of diphenylamine can be obtained by continued stripping or, alternatively, by secondary treatment with a more reactive olefin such as isobutylene or styrene. Preferably, the polyisobutylene should be incrementally added to the reaction mixture to control and maintain the desired reaction temperature and to minimize premature PIB isomerization to non-reactive olefins. However, depending on the desired product mixture it may be beneficial to add HR PIB oligomer to the reaction mixture all at once at a lower temperature than the reaction temperature.

If desired, the reaction can be carried out in a neutral solvent such as mineral oil or an inert hydrocarbon solvent, but generally no solvent is necessary.

Reaction time is a very flexible reaction parameter and is dependent on the reaction temperature, mole ratio of reactants and catalysts and pressure. Generally, the reaction will be carried out over a period of about 2 to 30 or more hours, preferably over a period of about 5 to 24 hours, and more preferably over a period of about 6 to 16 hours.

Upon completion of the reaction, the desired alkylated diphenylamine products can be isolated using conventional techniques, such as stripping under vacuum or separation by elution with hexane using column chromatography. Depending upon the particular reaction conditions selected the amount of monoalkylated DPA to dialkylated DPA in the product mixture can typically range from 34 to 68 mole % for the monoalkylate to 32 to 66 mole % for the dialkylate; however, under certain conditions the product mixture can be either predominantly monoalkylate or predominantly dialkylate. For example, in Example No. 13 shown in Table 2 below, the molar % ratio of monoalkylate to dialkylate was 44 to 56; in Example No. 3 shown in Table 1, below, the molar % ratio was 85 percent mono isomer and 15 percent dialkylated isomer; and in Example No. 1 shown in Table 1 the product contained exclusively mono isomer and a small amount of unreacted DPA. In all Examples 1–18 the alkylated products were liquid at room temperature (about 20° C.) and ambient pressure.

The following examples are presented to illustrate certain embodiments of this invention and are not to be construed as limiting the scope of the invention.

EXAMPLES

Representative experiments with HR PIB oligomers are summarized in Tables 1 and 2. These examples are exploratory in nature, designed to determine the scope of the alkylation reaction and do not necessarily represent optimum conditions for producing any particular product or composition. The runs in Tables 1 and 2 are arranged in chronological order, with the $C_{12}$ oligomers being listed first, followed by $C_{16}$, etc. Within each oligomer fraction, the runs are also arranged according to reaction temperature, with the lower temperature being listed first.

Examples 1–11

Alkylation of DPA with PIB Oligomers at Atmospheric Pressure

Table 1 describes the specific alkylation reaction conditions of Examples 1–11. Generally, each example was run according to the following procedure: Diphenylamine and F-24 (Engelhard) catalyst were added to a 300-mL, three-necked, round-bottom flask fitted with a mechanical stirrer, heating mantle, thermometer, condenser, nitrogen purge and an addition funnel. While stirring, the flask contents were heated to the temperatures shown in Table 1. When the indicated temperature was reached, PIB oligomer was incrementally added to the mixture over the times shown in Table 1 to control and maintain the desired reaction temperature. Following oligomer addition the reaction was continued at the temperatures and for the times shown in Table 1. Thereafter, the reaction product was cooled, then filtered over Celite under vacuum to separate the spent catalyst. The filtrate was analyzed, using GLC and $^1$H NMR, for DPA, monoalkylated DPA, dialkylated DPA and the distribution of individual isomers. In certain examples, the filtrate was stripped under vacuum to remove unreacted oligomers along with some DPA.

Reference is made to Example No. 6 in Table 1 as a specific representation of the above procedure. In this example, DPA (60 g) and F-24 catalyst (12 g, Engelhard) were heated to 170° C. in a glass flask, and PIB tetramer (C16) (199.3 g) [CMR (mole PIB tetramer/mole DPA)= 2.50] was added to the mixture over 46 minutes. The reaction was continued for 8 hours, cooled to room temperature and vacuum filtered over Celite. The filtrate was stripped by heating under high vacuum (1–2 mm Hg) to recover unreacted PIB tetramer and some DPA, to give a pale amber, liquid product. TBN, 136.5 mg KOH/g; 3.57% N; TBN/N, 38.2. Analysis by GLC: DPA, 5.3%; C4-DPA, 19.2%; C8-DPA, 16.1%; C12-DPA, 10.7%; C16-DPA, 36.6%; C20-DPA, 12.1%. $^1$H NMR: 5.55 ppm (>NH, monoalkylated DPA, 68%), 5.48 ppm (>NH, dialkylated DPA, 32%), and 5.70 ppm (>NH, free DPA, <<1%).

Similarly, in Examples 2 and 11 the reaction was subjected to two temperature regimens. Specifically, in Example 11 a commercial PIB distillate (95% purity, C8, 17.4%; C12, 39.8%; C16, 24.4%; C20, 12.9%; C24, 4.1%; and C28, 1.4%) was used without removal of about 5% process solvent. Diphenylamine (60 g) and F-24 catalyst (12 g, Engelhard) were added into a 300-mL, three-necked, round-bottomed flask fitted with a mechanical stirrer, heating mantle, thermometer, condenser, nitrogen purge, and addition funnel. The mixture was heated to 145° C. and PIB distillate (117.2 g) [CMR (mole PIB olig/mole DPA)=1.61] was added over 135 minutes and thereafter the reaction was continued for 90 min. A small amount of volatiles (~5 mL) was then removed using a Dean-Stark trap and reaction was continued for four hours at a temperature of 170° C. Finally, the reaction mixture was cooled to room temperature and vacuum filtered over Celite. Part of the filtrate (55 g) was eluted with hexane through a silica gel column to yield after rotaevaporation 18.6 g of unreacted olefin. The amine product was desorbed with hexane/ethyl ether (4:1), followed by ether, to give after rotaevaporation 30.9 g of a pale amber, liquid product (90% recovery). Analysis by GLC showed the following composition: DPA (18.2%), C4-DPA (28.2%), C8-DPA (18.7%), C12-DPA (12.7%), C16-DPA (8.7%), and C20-DPA (13.5%).

TABLE 1

Alkylation of DPA with HR PIB Oligomers at Atmospheric Pressure

| Example No. | PIB Fraction (% MV) | Temp. °C. | PIB Addn. Time min | Rxn. Time hr | CMR PIB/ DPA | DPA % conv. |
|---|---|---|---|---|---|---|
| 1 | C12(40) | 135 | 70 | 20 | 2.79 | 75 |
| 2 | C12(40) | 150 (170) | 22 | 13 (2) | 2.47 | 90 |
| 3 | C16(63) | 135 | 35 | 20 | 1.90 | 67 |
| 4 | C16(63) | 150 | 30 | 22 | 1.57 | 75 |
| 5 | C16(63) | 150 | 50 | 24 | 2.50 | 93 |
| 6 | C16(63) | 170 | 46 | 8 | 2.50 | 96 |
| 7 | C16(63) | 175 | 55 | 6 | 1.57 | 88 |
| 8 | C16(63) | 185 | 30 | 6 | 1.57 | 88 |
| 9 | C12/C16(53) | 175 | 96 | 6 | 2.31 | 91 |
| 10 | C20–28*(82) | 175 | 100 | 6 | 2.60 | 93 |
| 11 | C8–28(75)** | 145 (170) | 135 | 1.5 (4) | 1.61 | 82 |

*C20, 66.7%; C24, 23.1%; C28, 7.5%; C32, 2.7%
**C8, 17.4%; C12, 39.8%; C16, 24.4%; C20, 12.9%; C24, 4.1%; C28, 1.4%; in 5% process solvent.

Examples 12–18

Alkylation of DPA with HR PIB Oligomers under Nitrogen Pressure

Generally, Examples 12–18 as shown in Table 2 were carried out under nitrogen pressure in a 2-L, 316-stainless steel, mechanically stirred autoclave (Autoclave Engineers, Inc., Erie, Pa.). The autoclave was equipped with a heating mantle, cooling coil and a thermocouple. In a typical procedure, DPA and sulfuric acid-activated catalyst (F-24, Engelhardt) were charged to the autoclave, the autoclave was flushed and pressured with $N_2$, and heated to desired temperature under the reaction conditions set forth in Table 2. After PIB oligomer was added (Milroy mini pump), the reaction was continued for 24 h or less. The course of the reaction was monitored by GLC. After the reaction was completed the autoclave was cooled and its content filtered over Celite under vacuum to separate product from the catalyst. The filtrate was stripped by heating under high vacuum (1–2 mm Hg) to remove most of the unreacted oligomers and some DPA.

Example 18 is representative of the specific nitrogen pressure procedures. The autoclave was charged with DPA (240 g) and F-24 catalyst (48 g), nitrogen purged, pressured with nitrogen to 50 psi and heated to 165° C. Using a Milroy mini pump, PIB distillate (451.5 g, 95.5% purity, C8, 18.3%; C12, 41.0%; C16, 25.0%; C20, 10.5%; C24, 4.1%; and C28, 1.0%) [CMR (mole tetramer/mole DPA)=1.62] was incrementally added to the autoclave over 105 minutes to control and maintain the reaction temperature at 165° C. The reaction was thereafter continued at 165° C. for 16 hours and then allowed to cool. The product was vacuum filtered over Celite and the filtrate was stripped by heating under high vacuum (1–2 mm Hg) to give 457.7 g of a light amber, liquid product: TBN 156.3 mg KOH/g; 3.95% N; TBN/N, 39.6. Analysis by GLC: DPA, 2.7%; C4-DPA, 14.5%; C8-DPA, 26.1.0%; C12, 27.4%; C16, 20.0%; C20, 7.9%; and C24, 1.5%. $^1$H NMR: 5.56 ppm (>NH, monoalkylated DPA, 34%), 5.50 ppm (>NH, dialkylated DPA, 66%), and 5.67 ppm (>NH, free DPA, <1%).

TABLE 2

Alkylation of DPA with HR PIB Oligomers under 50 psi $N_2$

| Example No. | PIB Fraction (% MV) | Temp. ° C. | PIB Addn Time/ min | Rxn time hr | CMR PIB/ DPA | DPA % conv |
|---|---|---|---|---|---|---|
| 12 | C12(40) | 150 | 70 | 6 | 1.75 | 83 |
| 13 | C12(40) | 170 | 73 | 24 | 1.75 | 97 |
| 14 | C12(40) | 185(200) | 60 | 4.5 (0.5) | 1.76 | 99 |
| 15 | C8/C12(50) | 165 | 160 | 16 | 2.03 | 93 |
| 16 | C8/C12(50) | 175 | 100 | 6 | 2.01 | 89 |
| 17 | C8/C12/C16 (63) | 165 | 120 | 16 | 1.90 | 94 |
| 18 | C8–28(75) | 165 | 105 | 16 | 1.62 | 95 |

Additional reaction conditions for Examples 1–18 are found in Table 3. Oxidation studies of the products of selected Examples were carried out in a bulk oil oxidation bench test as described by E. S. Yamaguchi et al. in *Tribology Transactions*, Vol. 42(4), 895–901 (1999). In this test the rate of oxygen uptake at constant pressure by a given weight of oil was monitored. The time required (induction time) to take-up 250 mL $O_2$ per 25 g sample was measured, however results are reported as time for 1 L $O_2$ uptake per 100-g sample. The metals added as oil soluble naphthenates correspond to amounts found in the crankcase after the Sequence IIIE engine test. The selected oxidation bench test results are presented in Table 4.

TABLE 3

DPA ALKYLATION WITH PIB OLIGOMERS

| Example No. | wt, g DPA | Mole DPA | calc. avg. MW olig. | wt, g olig. | mole olig. | CMR (total mole olig./mole DPA) | Mole Fraction of Oligomer | | | | CMR: (mol olig. distribution/mole DPA) | | | |
|---|---|---|---|---|---|---|---|---|---|---|---|---|---|---|
| | | | | | | | $C_8$ | $C_{12}$ | $C_{16}$ | $C_{20-28}$ | $C_8$ | $C_{12}$ | $C_{16}$ | $C_{20-28}$ |
| Atmospheric Pressure | | | | | | | | | | | | | | |
| 1 | 60 | 0.355 | 168 | 166.4 | 0.990 | 2.79 | — | 1.0 | — | — | — | 2.79 | — | — |
| 2 | 60 | 0.355 | 168 | 149.1 | 0.890 | 2.47 | — | 1.0 | — | — | — | 2.47 | — | — |
| 3 | 50 | 0.296 | 224 | 126.2 | 0.563 | 1.90 | — | — | 1.0 | — | — | — | 1.9 | — |
| 4 | 60 | 0.355 | 224 | 125.0 | 0.558 | 1.57 | — | — | 1.0 | — | — | — | 1.57 | — |
| 5 | 60 | 0.355 | 224 | 199.3 | 0.890 | 2.50 | — | — | 1.0 | — | — | — | 2.50 | — |
| 6 | 60 | 0.355 | 224 | 199.3 | 0.890 | 2.50 | — | — | 1.0 | — | — | — | 2.50 | — |
| 7 | 60 | 0.355 | 224 | 125.0 | 0.558 | 1.57 | — | — | 1.0 | — | — | — | 1.57 | — |
| 8 | 60 | 0.355 | 224 | 125.0 | 0.558 | 1.57 | — | — | 1.0 | — | — | — | 1.57 | — |
| 9 | 60 | 0.355 | 194 | 158.9 | 0.819 | 2.31 | — | 0.59 | 0.41 | — | — | 1.36 | 0.95 | — |
| 10 | 50 | 0.296 | 309 | 228.3 | 0.771 | 2.60 | — | — | — | 1.0 | — | — | — | 2.6 |
| 11 | 60 | 0.355 | 196 | 111.7 | 0.570 | 1.61 | 0.27 | 0.41 | 0.19 | 0.13 | 0.43 | 0.66 | 0.31 | 0.21 |
| At 50 psi $N_2$ | | | | | | | | | | | | | | |
| 12 | 160 | 0.95 | 168 | 278 | 1.66 | 1.75 | — | 1.0 | — | — | — | 1.75 | — | — |
| 13 | 181 | 1.08 | 168 | 318 | 1.89 | 1.75 | — | 1.0 | — | — | — | 1.75 | — | — |
| 14 | 160 | 0.95 | 168 | 278 | 1.66 | 1.76 | — | 1.0 | — | — | — | 1.75 | — | — |
| 15 | 360 | 2.13 | 162 | 698 | 4.310 | 2.03 | 0.25 | 0.75 | — | — | 0.51 | 1.52 | — | — |
| 16 | 180 | 1.07 | 162 | 349 | 2.154 | 2.01 | 0.25 | 0.75 | — | — | 0.51 | 1.52 | — | — |
| 17 | 270 | 1.60 | 164 | 498.8 | 3.041 | 1.90 | 0.51 | 0.29 | 0.20 | — | 0.97 | 0.55 | 0.38 | — |
| 18 | 240 | 1.42 | 196 | 451.5 | 2.30 | 1.62 | 0.27 | 0.41 | 0.19 | 0.13 | 0.44 | 0.66 | 0.31 | 0.21 |

TABLE 4

Oxidation AO[1] Bench Test Results

| Sample ID | Base oil | TBN mgKOH/g | % N | TBN/N | RDPA wt % | mono/di ratio[2] | hr to 1L. O$_2$ uptake[3] |
|---|---|---|---|---|---|---|---|
| Reference | Grp 2 | — | — | — | none | none | 6.4 |
| Irganox L57[4] | Grp 2 | 181.6 | 4.63 | 39.2 | 0.10 | 52/48 | 13.8 |
| Naugalube 640[5] | Grp 2 | 175.9 | 4.58 | 38.4 | 0.10 | 55/45 | 13.9 |
| DPA | Grp 2 | 331.0 | 8.28 | 40.0 | 0.10 | none | 9.8 |
| Example 13 | Grp 2 | 172.7 | 4.67 | 37.0 | 0.10 | 44/56 | 15.4 |
| Example 5 | Grp 2 | 136.5 | 3.57 | 38.2 | 0.10 | 68/32 | 12.8 |
| Example 10 | Grp 2 | 90.6 | 2.44 | 37.2 | 0.10 | 57/43 | 10.3 |
| Example 18 | Grp 2 | 156.3 | 3.95 | 39.6 | 0.10 | 34/66 | 15.6 |
| Example 19 | Grp 2 | 157.2 | 3.97 | 39.6 | 0.10 | 58/42 | 13.2 |
| Reference | Grp 1 | — | — | — | none | none | 3.8 |
| Irganox L57 | Grp 1 | 181.6 | 4.63 | 39.2 | 0.10 | 52/48 | 5.4 |
| Naugalube 640 | Grp 1 | 175.9 | 4.58 | 38.4 | 0.10 | 55/45 | 5.1 |
| Example 13 | Grp 1 | 172.7 | 4.67 | 37.0 | 0.10 | 44/56 | 5.3 |
| Example 5 | Grp 1 | 136.5 | 3.57 | 38.2 | 0.10 | 68/32 | 4.7 |
| Example 18 | Grp 1 | 156.3 | 3.95 | 39.6 | 0.10 | 34/66 | 4.7 |
| Example 19 | Grp 1 | 157.2 | 3.97 | 39.6 | 0.10 | 58/42 | 4.9 |

Test conditions:
Temp. 171° C.;
Pressure, 1.0 atm O$_2$;
Stirrer, 1000 rev/min:
[1]Catalyst: Fe/Cu, 50/5 ppm;
Results:
±0.5 h.
[2]by $^{15}$N or $^1$H NMR.
[3]Screening formulation: [13 mM P/kg] ZnDTP, 6.0% Succinimide, [25] overbased Sulfonate, and [25] Calcium phenate in Group 1 or 2 base oil.
[4]Irganox ® L57 is available commercially from Ciba-Geigy.
[5]Naugalube ® 640 is available commercially from Crompton.

What is claimed is:

1. A process for alkylating diphenylamine, comprising:
   in one step reacting diphenylamine with a polyisobutylene in the presence of a suitable alkylation catalyst at a suitable alkylation reaction temperature less than about 200° C., wherein said polyisobutylene contains at least about 25% of a methylvinylidene isomer and wherein the number average molecular weight of said polyisobutylene is in the range of about 120 to about 600 and wherein the mole ratio of said polyisobutylene to said diphenylamine is in the range of 1.0:1.0 to 4.0:1.0 and
   forming an alkylated diphenylamine product wherein said alkylated diphenylamine product is liquid at room temperature and atmospheric pressure.

2. The process of claim 1 wherein the methylvinylidene content of the polyisobutylene is in the range of about 25% to about 95%.

3. The process of claim 1 wherein the methylvinylidene content of the polyisobutylene is in the range of about 40% to about 95%.

4. The process of claim 1 wherein the methylvinylidene content of the polyisobutylene is in the range of about 60% to about 90%.

5. The process of claim 1 wherein said clay catalyst is an acid activated clay catalyst.

6. The process of claim 1 wherein said reaction temperature is from about 125° C. to about 195° C.

7. The process of claim 6 wherein said reaction temperature is from about 135° C. to about 175° C.

8. The process of claim 6 wherein said reaction temperature is from about 155° C. to about 165° C.

9. The process of claim 1 wherein said mole ratio of said polyisobutylene:diphenylamine is from about 1.25:1 to about 3.0:1.

10. The process of claim 1 wherein said mole ratio of said polyisobutylene:diphenylamine is from about 1.5:1 to about 2.8:1.

11. The process of claim 1 wherein the average molecular weight of said polyisobutylene is in the range of about 150 to about 400.

12. The process of claim 1 wherein the average molecular weight of said polyisobutylene is in the range of about 160 to about 280.

13. The process of claim 1 wherein a reaction time is in the range of about five to 24 hours.

14. The process of claim 13 wherein said reaction time is in the range of about six to 16 hours.

15. The process of claim 1 wherein said polyisobutylene has a diisobutylene content in the range of about 10 percent to about 50 percent and wherein the mole ratio of diisobutylene:diphenylamine is less than about 0.6:1.

16. The process of claim 15 wherein said clay catalyst is an acid activated clay catalyst.

17. The process of claim 16 wherein said reaction temperature is from about 135° C. to about 175° C.

18. The process of claim 16 wherein said reaction temperature is from about 155° C. to about 165° C.

19. The process of claim 15 wherein the mole ratio of said diisobutylene:diphenylamine is less than about 0.55:1.

20. The process of claim 15 wherein the mole ratio of said diisobutylene:diphenylamine is less than about 0.45:1.

21. The process of claim 15 wherein said reaction time is in the range of about five to 24 hours.

22. The process of claim 21 wherein said reaction time is in the range of about six to 16 hours.

23. The process of claims 1 or 15 wherein said process forms a product mixture having 15 or more mole percent dialkylated diphenylamine and 34 or more mole percent monoalkylated diphenylamine.

24. A process for alkylating an aromatic amine, comprising:
   in one step reacting an aromatic amine with a polyisobutylene in the presence of a suitable alkylation catalyst at a suitable alkylation reaction temperature less than about 200° C., wherein said polyisobutylene contains at least about 25% of a methylvinylidene isomer and wherein the number average molecular weight of said polyisobutylene is in the range of about 120 to about 600 and wherein the mole ratio of said polyisobutylene to said aromatic amine is in the range of 1.0:1.0 to 4.0:1.0 and forming an alkylated aromatic amine product wherein said alkylated aromatic amine product is liquid at room temperature and atmospheric pressure.

25. The process of claim 24 wherein said aromatic amine is selected from the group consisting of N-phenyl-1-naphthylamine, N-phenyl-2-naphthylamine, p,p'-phenylenediamine, phenothiazine, phenoxazine, p-aminodiphenylamine, p-methylaminodiphenylamine and p-isopropylaminodiphenylamine.

26. An alkylated diphenylamine produced according to the process of claim 1.

27. An alkylated aromatic amine produced according to the process of claim 24.

* * * * *